United States Patent [19]

Li et al.

[11] Patent Number: 5,124,503
[45] Date of Patent: Jun. 23, 1992

[54] DICHLOROTRIFLUOROETHANE STABILIZED TO MINIMIZE HYDROLYSIS THEREOF

[75] Inventors: Chien C. Li, East Aurora; Kane D. Cook, Buffalo; Alfred A. Riederer, West Seneca, all of N.Y.

[73] Assignee: Allied-Signal Inc., Morris Township, Morris County, N.J.

[21] Appl. No.: 626,926

[22] Filed: Dec. 13, 1990

[51] Int. Cl.$^5$ .................. C07C 17/42; B01F 1/00; C23G 5/00
[52] U.S. Cl. .................. 570/110; 134/31; 134/40; 252/364
[58] Field of Search .................. 570/110

[56] References Cited

U.S. PATENT DOCUMENTS

| | | |
|---|---|---|
| 3,723,332 | 3/1973 | Barton .................. 570/110 |
| 3,974,230 | 8/1976 | Archer et al. .................. 570/110 |
| 4,378,303 | 3/1983 | Hisamoto et al. .................. 570/110 |

FOREIGN PATENT DOCUMENTS

| | | |
|---|---|---|
| 1-056630 | 3/1989 | Japan .................. 570/116 |
| 56631 | 3/1989 | Japan . |
| 56632 | 3/1989 | Japan . |
| 1-28943 | 5/1989 | Japan . |
| 1-28944 | 5/1989 | Japan . |
| 1-28945 | 5/1989 | Japan . |
| 1-39539 | 6/1989 | Japan . |
| 265042 | 10/1989 | Japan . |
| 1-268650 | 10/1989 | Japan .................. 570/110 |

*Primary Examiner*—J. E. Evans
*Attorney, Agent, or Firm*—Melanie L. Brown; Jay P. Friedenson

[57] ABSTRACT

The present invention provides stabilized compositions comprising dichlorotrifluoroethane and effective stabilizing amounts of alkanol having 4 or 5 carbon atoms, nitroalkane having 1 to 3 carbon atoms, and a third component of 1,2-epoxyalkane having 2 to 7 carbon atoms or phosphite ester. Stabilized dichlorotrifluoroethane is useful in a variety of vapor degreasing, cold cleaning, and solvent cleaning applications including defluxing.

21 Claims, No Drawings

DICHLOROTRIFLUOROETHANE STABILIZED TO MINIMIZE HYDROLYSIS THEREOF

FIELD OF THE INVENTION

The present invention relates to stabilized dichlorotrifluoroethane. Stabilized dichlorotrifluoroethane is useful in a variety of vapor degreasing, cold cleaning, and solvent cleaning applications including defluxing.

BACKGROUND OF THE INVENTION

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For difficult to remove soils where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned Part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancillary equipment.

Cold cleaning is another application where a number of solvents are used. In most cold cleaning applications, the soiled part is either immersed in the fluid or wiped with rags or similar objects soaked in solvents and allowed to air dry.

Fluorocarbon solvents, such as dichlorotrifluoroethane, have attained widespread use in recent years as effective, nontoxic, and nonflammable agents useful in degreasing applications and other solvent cleaning applications. Dichlorotrifluoroethane has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like.

The art is continually seeking new hydrochlorofluorocarbon solvents which offer alternatives for new and special applications for vapor degreasing and other cleaning applications. Solvents which are based on hydrochlorofluorocarbons are considered to be stratospherically safe substitutes for presently used fully halogenated chlorofluorocarbons. The latter are suspected of causing environmental problems in connection with the earth's protective ozone layer. Mathematical models have substantiated that hydrochlorofluorocarbons, such as dichlorotrifluoroethane, will not adversely affect atmospheric chemistry, being negligible contributors to ozone depletion and to green-house global warming in comparison to the fully halogenated species.

Hydrochlorofluorocarbons such as dichlorotrifluoroethane hydrolyze to form hydrogen chloride. While dichlorotrifluoroethane is useful as a cleaning solvent, the dichlorotrifluoroethane should be stabilized against possible changes during storage and use. When metallic materials are present such as occurs in many cleaning applications, the problem is worsened because the metal acts as a catalyst and causes the hydrolysis of dichlorotrifluoroethane to increase exponentially. Because metallic materials such as Al-2024 which is an aluminum based alloy having about 4.5% copper, copper, cold rolled steel, galvanized steel, stainless steel, and zinc are commonly used in cleaning apparatus, the hydrolysis problem is common. Also, ultraviolet light decomposes hydrochlorofluorocarbons such as dichlorotrifluoroethane.

In addition to hydrochlorofluorocarbons such as dichlorotrifluoroethane reacting with water to form acids such as hydrogen chloride and hydrogen fluoride, dichlorotrifluoroethane also reacts with alcoholic hydroxyl groups to form aldehydes and ketones. Known stabilizers for compositions of 1,1-dichloro-2,2,2-trifluoroethane and alcohol include: epoxy compounds as taught by Kokai Patent Publication No. 56,630 published Mar. 3, 1989; combinations of styrene and epoxy compounds as taught by Kokai Patent Publication No. 56,631 published Mar. 3, 1989; combinations of styrene compounds and phenols as taught by Kokai Patent Publication No. 56,632 published Mar. 3, 1989; combinations of epoxy and styrene compounds and phenols as taught by Kokai Patent Publication No. 128,943 published May 22, 1989; hydrocarbons containing nitro groups as taught by Kokai Patent Publication No. 128,944 published May 22, 1989; combinations of hydrocarbons containing nitro groups and epoxy compounds as taught by Kokai Patent Publication No. 128,945 published May 22, 1989; and phenols as taught by Kokai Patent Publication No. 265,042 published Oct. 23, 1989. Kokai Patent Publication No. 139,539 teaches 1,2-dichloro-1,1,2-trifluoroethane based azeotropic compositions which are stabilized with at least one of nitro compounds, phenols, amines, ethers, amylenes, esters, organic phosphites, epoxides, furans, alcohols, ketones, and triazoles.

Because dichlorotrifluoroethane may be used alone as a solvent, it would be advantageous to have a stabilized dichlorotrifluoroethane system which undergoes substantially no hydrolysis. This ideal stabilized dichlorotrifluoroethane system could then be used in commercial cleaning applications wherein a solvent is typically exposed to water, metallic materials, and ultraviolet light.

SUMMARY OF THE INVENTION

The present invention fills the need in the art by providing a composition comprising dichlorotrifluoroethane and effective stabilizing amounts of alkanol having 4 or 5 carbon atoms, nitroalkane having 1 to 3 carbon atoms, and a third component selected from the group consisting of 1,2-epoxyalkane having 2 to 7 carbon atoms and phosphite ester.

The present stabilized dichlorotrifluoroethane undergoes minimal hydrolysis and as such, can be used in cleaning applications wherein a solvent is typically exposed to water and metallic materials.

Other advantages of the present invention will become apparent from the following description.

DESCRIPTION OF THE INVENTION

The dichlorotrifluoroethane used can be one of its isomers: 1,1-dichloro-2,2,2-trifluoroethane (HCFC-123), 1,2-dichloro-1,1,2-trifluoroethane (HCFC-123a), or mixtures thereof in any proportions. Commercially available 1,1-dichloro-2,2,2-trifluoroethane can be used or a known process such as that taught by commonly assigned U.S. Pat. No. 4,145,368 can be used to produce 1,1-dichloro-2,2,2-trifluoroethane.

Examples of useful alkanols having 4 or 5 carbon atoms include 2-methyl-2-propanol; 2-methyl-2-butanol; 2-pentanol; 3-pentanol; and fluorinated tertiary alcohols of the Formula:

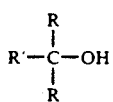

wherein each R is the same or different and is selected from the group consisting of $CF_3$, $CHF_2$, $CH_2F$, and $CH_3CF_2-$, and R' is an alkyl or fluoroalkyl group having 1 or 2 carbon atoms which are covered in commonly assigned Ser. No. 625,727 filed Dec. 4, 1990. The preferred alcohol is 3-pentanol.

Examples of useful nitroalkanes having 1 to 3 carbon atoms include nitromethane, nitroethane, 1-nitropropane, and 2-nitropropane. The preferred nitroalkanes are nitromethane and nitroethane.

Examples of useful 1,2-epoxyalkanes having 2 to 7 carbon atoms include epoxyethane; 1,2-epoxypropane; 1,2-epoxybutane; 2,3-epoxybutane; 1,2-epoxypentane; 2,3-epoxypentane; 1,2-epoxyhexane; and 1,2-epoxyheptane. The preferred 1,2-epoxyalkane is 1,2-epoxyhexane.

Examples of useful phosphite esters include diphenyl phosphite; triphenyl phosphite; triisodecyl phosphite; triisooctyl phosphite; and diisooctyl phosphite. The preferred phosphite esters are triisodecyl phosphite (hereinafter TDP) and triisooctyl phosphite (hereinafter TOP).

These materials are all known materials and most are commercially available.

The term "effective stabilizing amounts" as used herein means that amount of each of alkanol, nitroalkane, and 1,2-epoxyalkane or phosphite ester which in combination with the dichlorotrifluoroethane component allows the composition to be used and stored with minimal hydrolysis.

Preferably, the stabilized dichlorotrifluoroethane comprises from about 0.2 to about 1.2 percent by weight of alkanol, from about 0.1 to about 1.0 percent by weight of nitroalkane, and from about 0.2 to about 1.2 percent by weight of 1,2-epoxyalkane or phosphite ester. More preferably, the stabilized dichlorotrifluoroethane comprises from about 0.4 to about 0.8 percent by weight of alkanol, from about 0.2 to about 0.4 percent by weight of nitroalkane, and from about 0.4 to about 0.8 percent by weight of 1,2-epoxyalkane or phosphite ester.

When dichlorotrifluoroethane alone is in contact with Al-2024, the $Cl^-$ concentration is about 13 parts per million. When dichlorotrifluoroethane alone is in contact with Cu, the $Cl^-$ concentration is about 74 parts per million. When dichlorotrifluoroethane alone is in contact with CRS, the $Cl^-$ concentration is about 69 parts per million. When dichlorotrifluoroethane alone is in contact with GS, the $Cl^-$ concentration is about 5100 parts per million.

The stabilizers are effective in preventing the hydrolysis of the dichlorotrifluoroethane component in the Presence of Aluminum-2024, copper, cold rolled steel, galvanized steel, stainless steel 304, stainless steel 304L, stainless steel 316, and stainless steel 316L. Typically, as will be explained below, when the stabilized dichlorotrifluoroethane is in contact with metallic materials, the $Cl^-$ concentration is less than about 10 parts per million for Al-2024, about 20 parts per million for Cu, about 25 parts per million for CRS, and about 15 parts per million for GS. Also, the metallic surface remains shiny.

The stabilized dichlorotrifluoroethane of the present invention may be prepared in any known manner including weighing each component and then mixing the components together.

Stabilized dichlorotrifluoroethane is useful in a variety of vapor degreasing, cold cleaning, and solvent cleaning applications including defluxing.

The present stabilized dichlorotrifluoroethane may also be blended with at least one common solvent component such as other hydrochlorofluorocarbons, hydrofluorocarbons, alkanols having 1 or 2 carbon atoms, alkanes, and dichloroethylene. These other components may be used in amounts of up to about 50 weight percent based on the total weight of the stabilized dichlorotrifluoroethane and the at least one other component.

Examples of useful hydrochlorofluorocarbons include chlorodifluoromethane (known in the art as HCFC-22); 1,1-dichloro-1-fluoroethane (known in the art as HCFC-141b); 1-chloro-1,1-difluoroethane (known in the art as HCFC-142b); 2,2-dichloro-1,1,1,3,3-pentafluoropropane (known in the art as HCFC-225a);

1,2-dichloro-1,2,3,3,3-pentafluoropropane (known in the art as HCFC-225ba);

1,2-dichloro-1,1,2,3,3-pentafluoropropane (known in the art as HCFC-225bb);

1,1-dichloro-2,2,3,3,3-pentafluoropropane (known in the art as HCFC-225ca);

1,3-dichloro-1,1,2,2,3-pentafluoropropane (known in the art as HCFC-225cb);

1,1-dichloro-1,2,2,3,3-pentafluoropropane (known in the art as HCFC-225cc);

1,2-dichloro-1,1,3,3,3-pentafluoropropane (known in the art as HCFC-225d);

1,3-dichloro-1,1,2,3,3-pentafluoropropane (known in the art as HCFC-225ea); and 1,1-dichloro-1,2,3,3,3-pentafluoropropane (known in the art as HCFC-225eb).

Examples of useful hydrofluorocarbons include pentafluoroethane (known in the art as HFC-125); 1,1,1-trifluoroethane (known in the art as HFC-143a); and 1,1-difluoroethane (known in the art as HFC-152a).

Examples of useful alkanols having 1 or 2 carbon atoms are methanol and ethanol. Examples of useful alkanes include propane; butane; 2-methylpropane; pentane; 2-methylbutane; and 2,2-dimethylpropane. Examples of dichloroethylene are trans-1,2-dichloroethylene and cis-1,2-dichloroethylene.

In the process embodiment of the invention, the stabilized dichlorotrifluoroethane of the invention may be used to clean solid surfaces by treating the surfaces with the compositions in any manner well known in the art such as by dipping or spraying or use of conventional degreasing apparatus.

The present invention is more fully illustrated by the following non-limiting Examples.

EXAMPLES
COMPARATIVES

Seven day stability tests were done as follows:

Commercial grade HCFC-123 was saturated with water at room temperature. 125 ml of HCFC-123 was transferred into a 250 ml Pyrex flask which was connected to a water/glycol cooled condenser.

On top of the condenser, a "Drierite" desiccant was provided to prevent ambient moisture leaking into the solvent. A metal coupon was situated in the middle of the liquid-vapor phase. A total of eight common metal alloys were investigated. They are: Aluminum-2024(hereinafter Al-2024), Copper(hereinafter Cu), Cold Rolled steel(hereinafter CRS), and Galvanized Steel(hereinafter GS), SS 304, SS 304L, SS 316, and SS 316L.

The solvent then was under total reflux at its boiling temperature for seven days. Observation was made daily on the change of the metal surface including the loss of luster of the metal surface and stain or corrosion on the metal surface, if any and the solvent including coloration of the solvent, increased viscosity of the solvent and most importantly, the rate of change of the viscosity.

The pH values were determined for each solvent before and after the test. The Cl ion concentration in the solvent was determined by ion chromatography.

The pH was about 4.8 in the presence of Al-2024 and was about 3.5 in the presence of the other metals. The results are in Table I below. In Table I, S means stained, SC means slightly corroded, C means corroded, VC means very corroded, CL means colorless, and G means gray with suspended particles.

TABLE I

|         | Al-2024 | Cu  | CRS | GS   |
|---------|---------|-----|-----|------|
| Cl− (ppm) | 13      | 74  | 69  | 5100 |
| Metal   | S       | SC  | C   | VC   |
| Solvent | CL      | CL  | CL  | G    |

Dichlorotrifluoroethane was then combined with 0.4 weight percent of various stabilizers. Table II reports the results of dichlorotrifluoroethane with 3-pentanol alone. In Table II, S means stained, SS means slightly stained, C means corroded, CR means clear, and D means deposits.

TABLE II

|         | Al-2024 | Cu   | CRS  | GS   |
|---------|---------|------|------|------|
| Cl− (ppm) | 9.94    | 6.86 | 1.44 | 5.33 |
| Metal   | S       | SS   | C    | C    |
| Solvent | CR      | CR   | CR   | D    |

Table III reports the results of dichlorotrifluoroethane with 2-methyl-2-propanol alone. In Table III, S means stained, C means corroded, CR means clear, Y means yellow, and D means deposits.

TABLE III

|         | Al-2024 | Cu   | CRS  | GS     |
|---------|---------|------|------|--------|
| Cl− (ppm) | 2.58    | 3.74 | 10.0 | 506.93 |
| Metal   | S       | S    | C    | C      |
| Solvent | CR      | CR   | Y    | D      |

Table IV reports the results of dichlorotrifluoroethane with trifluoroethanol alone. In Table IV, SS means slightly stained, S means stained, C means corroded, CR means clear, Y means yellow, and D means deposits.

TABLE IV

|         | Al-2024 | Cu   | CRS  | GS   |
|---------|---------|------|------|------|
| Cl− (ppm) | 5.02    | 3.39 | 3.05 | 5.08 |
| Metal   | SS      | S    | C    | C    |
| Solvent | CR      | CR   | Y    | D    |

Table V reports the results of dichlorotrifluoroethane with trimethylene oxide alone. In Table V, S means stained, C means corroded, CR means clear, Y means yellow, and D means deposits.

TABLE V

|         | Al-2024 | Cu    | CRS  | GS    |
|---------|---------|-------|------|-------|
| Cl− (ppm) | 4.82    | 11.31 | 7.78 | 42.44 |
| Metal   | S       | C     | C    | C     |
| Solvent | CR      | CR    | Y    | D     |

Table VI reports the results of dichlorotrifluoroethane with 0.2 wt. % of nitroethane alone. In Table VI, S means stained, C means corroded, and CR means clear.

TABLE VI

|         | Al-2024 | Cu   | CRS  | GS   |
|---------|---------|------|------|------|
| Cl− (ppm) | 8.72    | 7.70 | 5.65 | 6.59 |
| Metal   | S       | S    | C    | S    |
| Solvent | CR      | CR   | CR   | CR   |

Table VII reports the results of dichlorotrifluoroethane with 0.2 wt. % of nitromethane alone. In Table VII, S means stained, C means corroded, and CR means clear.

TABLE VII

|         | Al-2024 | Cu   | CRS  | GS   |
|---------|---------|------|------|------|
| Cl− (ppm) | 9.51    | 8.05 | 5.12 | 7.25 |
| Metal   | S       | S    | C    | S    |
| Solvent | CR      | CR   | CR   | CR   |

Table VIII reports the results of dichlorotrifluoroethane with 0.4 wt. % of epoxyhexane and 0.2 wt. % of nitromethane. In table VIII, SS means slightly stained, S means stained, and CR means clear.

TABLE VIII

|         | Al-2024 | Cu   | CRS  | GS   |
|---------|---------|------|------|------|
| Cl− (ppm) | 1.48    | 1.41 | 2.85 | 3.23 |
| Metal   | SS      | SS   | S    | S    |
| Solvent | CR      | CR   | CR   | CR   |

Table IX reports the results of dichlorotrifluoroethane with 0.4 wt. % of epoxybutane and 0.2 wt. % of nitromethane. In Table IX, SS means slightly stained, S means stained, and CR means clear.

TABLE IX

|  | Al-2024 | Cu | CRS | GS |
|---|---|---|---|---|
| Cl⁻ (ppm) | 1.48 | 1.41 | 2.85 | 3.23 |
| Metal | SS | SS | S | SS |
| Solvent | CR | CR | CR | CR |

EXAMPLE 1

The procedure for the Comparative above was repeated except that commercial grade HCFC-123 having 0.4 wt. % of 3-pentanol, 0.4 wt. % of triisodecylphosphite, and 0.2 wt. % of nitromethane therein was used.

The pH for all of the tests ranged from 5.0 to 6.5. The results are in Table X below. In Table X, Sol means Solvent, NC means no change, CL means colorless, and NV means nonviscous. ** means that the solvent dried up.

TABLE X

|  | Al | Cu | CRS | GS | SS304 | SS304L | SS316 | SS316L |
|---|---|---|---|---|---|---|---|---|
| Cl⁻ (ppm) | 2.63 | 1.28 | 14 ** | 5.39 | 29.17 ** | 7.03 | 5.83 | 4.37 |
| Metal | NC | NC | NC | NC | NC | NC | NC | NC |
| Sol | CL/NV | CL/NV | CL/NV | CL/NV | CL/NV | CL/NV | CL/NV | CL/NV |

EXAMPLE 2

The procedure for the Comparative above was repeated except that commercial grade HCFC-123 having 0.4 wt. % of 1,2-epoxybutane, 0.4 wt. % of 2-methyl-2-propanol, and 0.2 wt. % of nitromethane therein was used.

The pH for these tests ranged from 4.8 to 6.2. The results are in Table XI below. In Table XI, Sol means Solvent, NC means no change, SS means slightly stained, CL means colorless, and NV means nonviscous. ** means that that solvent dried up.

TABLE XI

|  | Al | Cu | CRS | GS | SS304 | SS304L | SS316 | SS316L |
|---|---|---|---|---|---|---|---|---|
| Cl⁻ (ppm) | 1.72 ** | 8.88 ** | 6.91 | 4.54 | 3.85 | 4.95 | 8.68 | 2.87 |
| Metal | NC | NC | SS | NC | NC | NC | NC | NC |
| Sol | CL/NV | CL/NV | CL/NV | CL/NV | CL/NV | CL/NV | CL/NV | CL/NV |

EXAMPLE 3

The procedure for the Comparative above was repeated except that commercial grade HCFC-123 having 0.4 wt. % of 1,2-epoxyhexane, 0.4 wt. % of 2-methyl-2-propanol, and 0.2 wt. % of nitromethane therein was used.

The results are in Table XII below. In Table XII, S means stained and CR means clear.

TABLE XII

|  | Al-2024 | Cu | CRS | GS |
|---|---|---|---|---|
| Cl⁻ (ppm) | 17.55 | 18.38 | 24.06 | 11.68 |
| Metal | S | S | S | S |
| Solvent | CR | CR | CR | CR |

EXAMPLE 4

The procedure for the Comparative above was repeated except that commercial grade HCFC-123 having 0.4 wt. % of TDP, 0.4 wt. % of 2-methyl-2-propanol, and 0.2 wt. % of nitromethane therein was used.

The results are in Table XIII below. In Table XIII, SS means slightly stained, NC means no change, and CR means clear.

TABLE XIII

|  | Al-2024 | Cu | CRS | GS |
|---|---|---|---|---|
| Cl⁻ (ppm) | 6.97 | 1.32 | 2.41 | 5.05 |
| Metal | SS | NC | SS | SS |
| Solvent | CR | CR | CR | CR |

EXAMPLE 5

The procedure for the Comparative above was repeated except that commercial grade HCFC-123 having 0.4 wt. % of TDP, 0.4 wt. % of 2-methyl-2-propanol, 0.4 wt. % of epoxyhexane, and 0.2 wt. % of nitromethane therein was used.

The results are in Table XIV below. In Table XIV, NC means no change, S means stained, and CR means clear.

TABLE XIV

|  | Al-2024 | Cu | CRS | GS |
|---|---|---|---|---|
| Cl⁻ (ppm) | 1.17 | 1.03 | 1.00 | lost |
| Metal | NC | S | S | S |
| Solvent | CR | CR | CR | CR |

EXAMPLES 6-203

Example 1 is repeated using HCFC-123 with the stabilizer systems in Table XV. In Table XV, the abbreviations are as follows: 2-methyl-2-propanol(MP), 2-methyl-2-butanol(MB), 2-pentanol(2-P), 3-Pentanol(3-P), nitromethane(NM), nitroethane(NE), 1-nitropropane(1-N), 2-nitropropane(2-N), epoxyethane(EE), 1,2-epoxypropane(EP), 1,2-epoxybutane(1,2-EB), 2,3-epoxybutane(2,3-EB), 1,2-epoxypentane(1,2-EP), 2,3-epoxypentane(2,3-EP), 1,2-epoxyhexane(1,2-EHX), 1,2-epoxyheptane(1,2-EHP), diphenyl phosphite(DPP), triphenyl phosphite(TPP), triisodecyl phosphite(TDP), triisooctyl phosphite(TOP), and diisooctyl phosphite(DOP).

TABLE XV

| Example | Alkanol | Nitroalkane | Epoxyalkane | Phosphite Ester |
|---|---|---|---|---|
| 6 | MP | NM | EE | — |
| 7 | MP | NM | EP | — |
| 8 | MP | NM | 2,3-EB | — |
| 9 | MP | NM | 1,2-EP | — |
| 10 | MP | NM | 2,3-EP | — |
| 11 | MP | NM | 1,2-EHP | — |
| 12 | MP | NM | — | DPP |
| 13 | MP | NM | — | TPP |
| 14 | MP | NM | — | TOP |
| 15 | MP | NM | — | DOP |
| 16 | MB | NM | EE | — |
| 17 | MB | NM | EP | — |
| 18 | MB | NM | 1,2-EB | — |
| 19 | MB | NM | 2,3-EB | — |
| 20 | MB | NM | 1,2-EP | — |
| 21 | MB | NM | 2,3-EP | — |
| 22 | MB | NM | 1,2-EHX | — |
| 23 | MB | NM | 1,2-EHP | — |
| 24 | MB | NM | — | DPP |
| 25 | MB | NM | — | TPP |
| 26 | MB | NM | — | TDP |
| 27 | MB | NM | — | TOP |
| 28 | MB | NM | — | DOP |
| 29 | 2-P | NM | EE | — |
| 30 | 2-P | NM | EP | — |
| 31 | 2-P | NM | 1,2-EB | — |
| 32 | 2-P | NM | 2,3-EB | — |
| 33 | 2-P | NM | 1,2-EP | — |
| 34 | 2-P | NM | 2,3-EP | — |
| 35 | 2-P | NM | 1,2-EHX | — |
| 36 | 2-P | NM | 1,2-EHP | — |
| 37 | 2-P | NM | — | DPP |
| 38 | 2-P | NM | — | TPP |
| 39 | 2-P | NM | — | TDP |
| 40 | 2-P | NM | — | TOP |
| 41 | 2-P | NM | — | DOP |
| 42 | 3-P | NM | EE | — |
| 43 | 3-P | NM | EP | — |
| 44 | 3-P | NM | 1,2-EB | — |
| 45 | 3-P | NM | 2,3-EB | — |
| 46 | 3-P | NM | 1,2-EP | — |
| 47 | 3-P | NM | 2,3-EP | — |
| 48 | 3-P | NM | 1,2-EHX | — |
| 49 | 3-P | NM | 1,2-EHP | — |
| 50 | 3-P | NM | — | DPP |
| 51 | 3-P | NM | — | TPP |
| 52 | 3-P | NM | — | TOP |
| 53 | 3-P | NM | — | DOP |
| 54 | MP | NE | EE | — |
| 55 | MP | NE | EP | — |
| 56 | MP | NE | 2,3-EB | — |
| 57 | MP | NE | 1,2-EP | — |
| 58 | MP | NE | 2,3-EP | — |
| 59 | MP | NE | 1,2-EHX | — |
| 60 | MP | NE | 1,2-EHP | — |
| 61 | MP | NE | — | DPP |
| 62 | MP | NE | — | TPP |
| 63 | MP | NE | — | TDP |
| 64 | MP | NE | — | TOP |
| 65 | MP | NE | — | DOP |
| 66 | MB | NE | EE | — |
| 67 | MB | NE | EP | — |
| 68 | MB | NE | 1,2-EB | — |
| 69 | MB | NE | 2,3-EB | — |
| 70 | MB | NE | 1,2-EP | — |
| 71 | MB | NE | 2,3-EP | — |
| 72 | MB | NE | 1,2-EHX | — |
| 73 | MB | NE | 1,2-EHP | — |
| 74 | MB | NE | — | DPP |
| 75 | MB | NE | — | TPP |
| 76 | MB | NE | — | TDP |
| 77 | MB | NE | — | TOP |
| 78 | MB | NE | — | DOP |
| 79 | 2-P | NE | EE | — |
| 80 | 2-P | NE | EP | — |
| 81 | 2-P | NE | 1,2-EB | — |
| 82 | 2-P | NE | 2,3-EB | — |
| 83 | 2-P | NE | 1,2-EP | — |
| 84 | 2-P | NE | 2,3-EP | — |
| 85 | 2-P | NE | 1,2-EHX | — |
| 86 | 2-P | NE | 1,2-EHP | — |
| 87 | 2-P | NE | — | DPP |
| 88 | 2-P | NE | — | TPP |
| 89 | 2-P | NE | — | TDP |
| 90 | 2-P | NE | — | TOP |
| 91 | 2-P | NE | — | DOP |
| 92 | 3-P | NE | EE | — |
| 93 | 3-P | NE | EP | — |
| 94 | 3-P | NE | 1,2-EB | — |
| 95 | 3-P | NE | 2,3-EB | — |
| 96 | 3-P | NE | 1,2-EP | — |
| 97 | 3-P | NE | 2,3-EP | — |
| 98 | 3-P | NE | 1,2-EHX | — |
| 99 | 3-P | NE | 1,2-EHP | — |
| 100 | 3-P | NE | — | DPP |
| 101 | 3-P | NE | — | TPP |
| 102 | 3-P | NE | — | TOP |
| 103 | 3-P | NE | — | DOP |
| 104 | MP | 1-N | EE | — |
| 105 | MP | 1-N | EP | — |
| 106 | MP | 1-N | 2,3-EB | — |
| 107 | MP | 1-N | 1,2-EP | — |
| 108 | MP | 1-N | 2,3-EP | — |
| 109 | MP | 1-N | 1,2-EHX | — |
| 110 | MP | 1-N | 1,2-EHP | — |
| 111 | MP | 1-N | — | DPP |
| 112 | MP | 1-N | — | TPP |
| 113 | MP | 1-N | — | TDP |
| 114 | MP | 1-N | — | TOP |
| 115 | MP | 1-N | — | DOP |
| 116 | MB | 1-N | EE | — |
| 117 | MB | 1-N | EP | — |
| 118 | MB | 1-N | 1,2-EB | — |
| 119 | MB | 1-N | 2,3-EB | — |
| 120 | MB | 1-N | 1,2-EP | — |
| 121 | MB | 1-N | 2,3-EP | — |
| 122 | MB | 1-N | 1,2-EHX | — |
| 123 | MB | 1-N | 1,2-EHP | — |
| 124 | MB | 1-N | — | DPP |
| 125 | MB | 1-N | — | TPP |
| 126 | MB | 1-N | — | TDP |
| 127 | MB | 1-N | — | TOP |
| 128 | MB | 1-N | — | DOP |
| 129 | 2-P | 1-N | EE | — |
| 130 | 2-P | 1-N | EP | — |
| 131 | 2-P | 1-N | 1,2-EB | — |
| 132 | 2-P | 1-N | 2,3-EB | — |
| 133 | 2-P | 1-N | 1,2-EP | — |
| 134 | 2-P | 1-N | 2,3-EP | — |
| 135 | 2-P | 1-N | 1,2-EHX | — |
| 136 | 2-P | 1-N | 1,2-EHP | — |
| 137 | 2-P | 1-N | — | DPP |
| 138 | 2-P | 1-N | — | TPP |
| 139 | 2-P | 1-N | — | TDP |
| 140 | 2-P | 1-N | — | TOP |
| 141 | 2-P | 1-N | — | DOP |
| 142 | 3-P | 1-N | EE | — |
| 143 | 3-P | 1-N | EP | — |
| 144 | 3-P | 1-N | 1,2-EB | — |
| 145 | 3-P | 1-N | 2,3-EB | — |
| 146 | 3-P | 1-N | 1,2-EP | — |
| 147 | 3-P | 1-N | 2,3-EP | — |
| 148 | 3-P | 1-N | 1,2-EHX | — |
| 149 | 3-P | 1-N | 1,2-EHP | — |
| 150 | 3-P | 1-N | — | DPP |
| 151 | 3-P | 1-N | — | TPP |
| 152 | 3-P | 1-N | — | TOP |
| 153 | 3-P | 1-N | — | DOP |
| 154 | MP | 2-N | EE | — |
| 155 | MP | 2-N | EP | — |
| 156 | MP | 2-N | 2,3-EB | — |
| 157 | MP | 2-N | 1,2-EP | — |
| 158 | MP | 2-N | 2,3-EP | — |
| 159 | MP | 2-N | 1,2-EHX | — |
| 160 | MP | 2-N | 1,2-EHP | — |
| 161 | MP | 2-N | — | DPP |
| 162 | MP | 2-N | — | TPP |
| 163 | MP | 2-N | — | TDP |
| 164 | MP | 2-N | — | TOP |
| 165 | MP | 2-N | — | DOP |
| 166 | MB | 2-N | EE | — |
| 167 | MB | 2-N | EP | — |

TABLE XV-continued

| Example | Alkanol | Nitroalkane | Epoxyalkane | Phosphite Ester |
|---|---|---|---|---|
| 168 | MB | 2-N | 1,2-EB | — |
| 169 | MB | 2-N | 2,3-EB | — |
| 170 | MB | 2-N | 1,2-EP | — |
| 171 | MB | 2-N | 2,3-EP | — |
| 172 | MB | 2-N | 1,2-EHX | — |
| 173 | MB | 2-N | 1,2-EHP | — |
| 174 | MB | 2-N | — | DPP |
| 175 | MB | 2-N | — | TPP |
| 176 | MB | 2-N | — | TDP |
| 177 | MB | 2-N | — | TOP |
| 178 | MB | 2-N | — | DOP |
| 179 | 2-P | 2-N | EE | — |
| 180 | 2-P | 2-N | EP | — |
| 181 | 2-P | 2-N | 1,2-EB | — |
| 182 | 2-P | 2-N | 2,3-EB | — |
| 183 | 2-P | 2-N | 1,2-EP | — |
| 184 | 2-P | 2-N | 2,3-EP | — |
| 185 | 2-P | 2-N | 1,2-EHX | — |
| 186 | 2-P | 2-N | 1,2-EHP | — |
| 187 | 2-P | 2-N | — | DPP |
| 188 | 2-P | 2-N | — | TPP |
| 189 | 2-P | 2-N | — | TDP |
| 190 | 2-P | 2-N | — | TOP |
| 191 | 2-P | 2-N | — | DOP |
| 192 | 3-P | 2-N | EE | — |
| 193 | 3-P | 2-N | EP | — |
| 194 | 3-P | 2-N | 1,2-EB | — |
| 195 | 3-P | 2-N | 2,3-EB | — |
| 196 | 3-P | 2-N | 1,2-EP | — |
| 197 | 3-P | 2-N | 2,3-EP | — |
| 198 | 3-P | 2-N | 1,2-EHX | — |
| 199 | 3-P | 2-N | 1,2-EHP | — |
| 200 | 3-P | 2-N | — | DPP |
| 201 | 3-P | 2-N | — | TPP |
| 202 | 3-P | 2-N | — | TOP |
| 203 | 3-P | 2-N | — | DOP |

EXAMPLE 204–406

Examples 1 through 203 are repeated except that HCFC-123a is used.

EXAMPLES 407–609

Examples 1 through 203 are repeated except that a mixture of HCFC-123 and HCFC-123a is used.

EXAMPLES 610–1,218

Each of the stabilized dichlorotrifluoroethane compositions of Examples 1 through 609 is combined with up to 50 weight percent of 1,1-dichloro-1-fluoroethane to form a solvent blend.

Having described the invention in detail and by reference to preferred embodiments thereof, it will be apparent that modifications and variations are possible without departing from the scope of the invention defined in the appended claims.

What is claimed is:

1. Stabilized compositions comprising dichlorotrifluoroethane and from about 0.2 to about 1.2 weight percent of alkanol having 4 or 5 carbon atoms, from about 0.1 to about 1.0 weight percent of nitroalkane having 1 to 3 carbon atoms, and from about 0.2 to about 1.2 weight percent of 1,2-epoxyalkane having 2 to 7 carbon atoms.

2. The stabilized compositions of claim 1 wherein said dichlorotrifluoroethane is 1,1-dichloro-2,2,2-trifluoroethane.

3. The stabilized compositions of claim 1 wherein said dichlorotrifluoroethane is 1,2-dichloro-1,1,2-trifluoroethane.

4. The stabilized compositions of claim 1 wherein said dichlorotrifluoroethane is a mixture of 1,1-dichloro-2,2,2-trifluoroethane and 1,2-dichloro-1,1,2-trifluoroethane.

5. The stabilized compositions of claim 1 wherein said alkanol is an alkanol selected from the group consisting of 2-methyl-2-propanol, 2-methyl-2-butanol, 2-pentanol, and 3-pentanol.

6. The stabilized compositions of claim 1 wherein said nitroalkane is a nitroalkane selected from the group consisting of nitromethane, nitroethane, 1-nitropropane, and 2-nitropropane.

7. The stabilized compositions of claim 1 wherein said 1,2-epoxyalkane is a 1,2-epoxyalkane selected from the group consisting of epoxyethane; 1,2-epoxypropane; 1,2-epoxybutane; 2,3-epoxybutane; 1,2-epoxypentane; 2,3-epoxypentane; 1,2-epoxyhexane; and 1,2-epoxyheptane.

8. The stabilized compositions of claim 5, wherein said alkanol is 3-pentanol.

9. The stabilized compositions of claim 6 wherein said nitroalkane is selected from the group consisting of nitromethane and nitroethane.

10. The stabilized compositions of claim 7 wherein said 1,2-epoxyalkane is 1,2-epoxyhexane.

11. A solvent composition consisting essentially of the stabilized compositions of claim 1.

12. Stabilized compositions comprising dichlorotrifluoroethane and from about 0.2 to about 1.2 weight percent of alkanol having 4 or 5 carbon atoms, from about 0.1 to about 1.0 weight percent of nitroalkane having 1 to 3 carbon atoms, and from about 0.2 to about 1.2 weight percent of phosphite ester.

13. The stabilized compositions of claim 12 wherein said dichlorotrifluoroethane is 1,1-dichloro-2,2,2-trifluoroethane.

14. The stabilized compositions of claim 12 wherein said dichlorotrifluoroethane is 1,2-dichloro-1,1,2-trifluoroethane.

15. The stabilized compositions of claim 12 wherein said dichlorotrifluoroethane is a mixture of 1,1-dichloro-2,2,2-trifluoroethane and 1,2-dichloro-1,1,2-trifluoroethane.

16. The stabilized compositions of claim 12 wherein said alkanol is an alkanol selected from the group consisting of 2-methyl-2-propanol, 2-methyl-2-butanol, 2-pentanol, and 3-pentanol.

17. The stabilized compositions of claim 12 wherein said nitroalkane is a nitroalkane selected from the group consisting of nitromethane, nitroethane, 1-nitropropane, and 2-nitropropane.

18. The stabilized compositions of claim 12 wherein said phosphite ester is a phosphite ester selected from the group consisting of diphenyl phosphite; triphenyl phosphite; triisodecyl phosphite; triisooctyl phosphite; and diisooctyl phosphite.

19. The stabilized compositions of claim 12 wherein said alkanol is 3-pentanol.

20. The stabilized compositions of claim 12 wherein said nitroalkane is selected from the group consisting of nitromethane and nitroethane.

21. The stabilized compositions of claim 12 wherein said phosphite ester is selected from the group consisting of triisodecyl phosphite and triisooctyl phosphite.

* * * * *